United States Patent [19]

Fleck et al.

[11] 4,006,158
[45] Feb. 1, 1977

[54] FLUORESCENT 1,2,3-TRIAZOLE DERIVATIVES OF 3-PHENYLCOUMARIN

[75] Inventors: Fritz Fleck, Bottmingen; Hans Balzer, Munchenstein; Horst Aebli, Basel, all of Switzerland

[73] Assignee: Sandoz Ltd., Basel, Switzerland

[22] Filed: Apr. 28, 1975

[21] Appl. No.: 572,005

Related U.S. Application Data

[63] Continuation of Ser. No. 695,330, Jan. 3, 1968, abandoned.

[30] Foreign Application Priority Data

Jan. 5, 1967    Switzerland ................... 108/67

[52] U.S. Cl. .................. 260/308 B; 106/21; 252/301.17; 252/301.29; 260/240 D; 260/240 G; 260/308 A
[51] Int. Cl.² .............. C07D 405/04; C07D 405/10
[58] Field of Search ................... 260/308 A, 308 B

[56] References Cited

UNITED STATES PATENTS 3,646,052   2/1972   Neuner et al. ................ 260/308 A
3,784,569   1/1974   Kirchmayr et al. ............ 260/308 A Primary Examiner—Alton D. Rollins
Attorney, Agent, or Firm—Gerald D. Sharkin; Richard E. Vila

[57] ABSTRACT

Polyester, cotton, polyamide and polyacrylonitrile fabrics and foils of polyvinylchloride are optically brightened by the addition of a compound of the formula

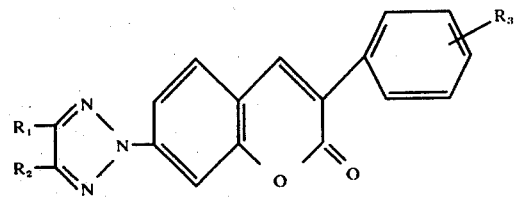

in which each of
  $R_1$ and $R_2$ represents a hydrogen atom or an aliphatic, alicyclic, araliphatic, halogen- or alkyl-substituted araliphatic, aromatic, or halogen- or alkyl-substituted aromatic radical,
or
  $R_1$ and $R_2$ together with the two carbon atoms of the triazole ring form a five or six membered cycloalkyl ring or such a cycloalkyl ring having condensed on it a benzene ring,
  $R_3$ represents a hydrogen or halogen atom or a low molecular weight alkyl or alkoxy radical.

1 Claim, No Drawings

FLUORESCENT 1,2,3-TRIAZOLE DERIVATIVES OF 3-PHENYLCOUMARIN

This is a continuation of application Ser. No. 695,330, filed Jan. 3, 1968, now abandoned.

BACKGROUND OF THE INVENTION

In comparison to the known 1,2,3-triazole derivatives of 3-phenyl-7-aminocoumarin described in French Pat. No. 1,358,820, the triazoles of the invention are characterized by more neutral shades of white and a better solubility in organic media. They are excellently fast to light and stable to heat and also stable towards neutral or acid bleaching agent solutions.

SUMMARY OF THE INVENTION

The present invention provides compounds of the formula I

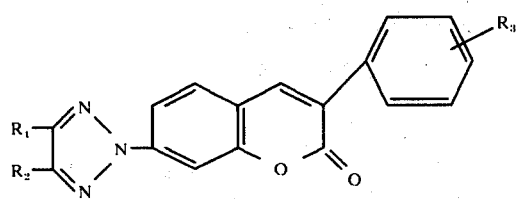

in which each of $R_1$ and $R_2$ represents a hydrogen atom or an aliphatic, alicyclic, araliphatic, halogen or alkyl substituted araliphatic, aromatic, or halogen or alkyl substituted aromatic radical, or $R_1$ and $R_2$ together with the two carbon atoms of the triazole ring form a five or six membered cycloalkyl ring or such a cycloalkyl ring having condensed on it a benzene ring, $R_3$ represents a hydrogen or halogen atom or a low molecular weight alkyl or alkoxy radical; the phrase "low molecular weight" as applied to alkyl and alkoxy designates such radicals with 1 to 6 carbon atoms. The compounds of formula I fluoresce when in solution.

The present invention also provides a process for the production of the compounds of formula I, characterized in that a hydrazone oxime of the formula II

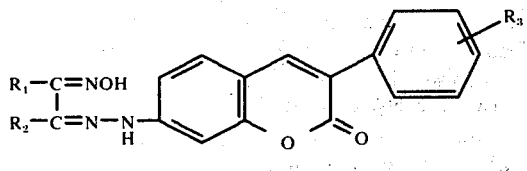

wherein $R_1$, $R_2$ and $R_3$ have the above significance, is cyclized to give a 1,2,3-triazole compound by heating in the presence of a solvent and an anhydride of a low molecular weight fatty acid; said anhydrides are those containing up to 12 carbon atoms. Preferably this heating is effected in the presence of a tertiary base.

Specific examples of suitable radicals $R_1$ and $R_2$ are: hydrogen, methyl, ethyl, isopropyl, phenyl, diphenyl, benzyl, tolyl, methoxyphenyl, butyl, chlorophenyl, chlorotolyl, styryl, chlorostyryl, cyclohexyl, cyclopentyl, naphthyl, xylyl, dichlorophenyl, nonyl, cetyl, stearyl, dimethylbenzyl. As pointed out above, the radicals $R_1$ and $R_2$ can also be part of a cycloalkyl ring, which cycloalkyl ring may have condensed on it a benzene ring, thus forming part of a, e.g., cyclopentyl, cyclohexyl or benzocyclohexyl (i.e. tetralyl) radical.

Suitable values for the radical $R_3$ are hydrogen, methyl, ethyl, butyl, isopropyl, methoxy, ethoxy, chlorine or bromine.

The starting material hydrazone oximes of the formula II may be produced in known manner, for example by reacting α-nitrosoketones with 3-phenyl-7-hydrazino-coumarin which may be substituted if necessary.

As indicated above, when $R_1$ or $R_2$ represents an aromatic or araliphatic radical, the aromatic or araliphatic radical may be substituted with alkyl (for example methyl) or halogen (especially chlorine), or both alkyl and halogen.

The processes hitherto described in the literature on the subject for cyclizing hydrazone oximes give rise to bad yields in cyclization product. It is therefore surprising that the compounds of formula I can be obtained with good yields merely by heating, as described in detail hereinafter, a hydrazone oxime of the formula II with, for example, acetic anhydride in the presence of a solvent and optionally of a tertiary base. The compounds of formula I can be freed of by-products and purified in manner known per se.

Suitable anhydrides of low molecular weight fatty acids for use in the process of the invention are those of acetic acid and propionic acid; suitable solvents are, for example, dimethylformamide, dimethylacetamide, dimethylsulphoxide, N-methylpyrrolidone and cyclohexanone. The solvent is used, depending on the solubility of the hydrazone oxime, in an amount which generally comes to three to five times the quantity of hydrazone oxime. Suitable tertiary bases the presence of which favourably influences the reaction are, for example pyridine or technical mixtures of pyridine bases. The fatty acid anhydride and the tertiary base are used in excess, it being permissible for the weight ratios to vary within wide limits.

Temperatures favourable for effecting the reaction of the process of the invention are between 50° and 200° C, preferably between 100° and 150° C.

The compounds of formula I are colourless or almost colourless substances which, when dissolved in a solvent therefor, strongly fluoresce violet-blue to blue; the compounds of formula I are exceedingly suitable as optical brighteners or marking agents for organic materials or as scintillating agents.

Organic materials, which may be optically brightened by the compounds of formula I, are primarily those of synthetic, fibre forming polyesters, polyamides, polyurethanes, polyolefins, polyvinylchloride, polyvinylidenechloride, polyacrylonitrile, modified polyacrylonitrile, cellulose triacetate or diacetate, further also oils, fats, waxes, lacquers, resins and cosmetic preparations.

The compounds of formula I can be used dissolved in solvents or in finely divided form, for example as aqueous dispersions, when they are to be used in the treatment of textile materials. They can be successfully incorporated into spinning or pressing masses or may be added to monomers or a pre-condensate used for the production of plastics. Their use with polyester or mixed polyester fabrics is advantageously affected by padding in an aqueous dispersion of the new compounds, whereupon drying and thermal fixing are effected. The concentration of the new compounds, depending on the manner of their use, may amount to 0.01 to 0.5%, based on the weight of the material to be brightened. The brighteners produced according to the invention may be used alone or in combination with other brighteners, as well as in the presence of surface active agents, for instance washing agents or in the presence of bleaching agents.

In the following Examples the temperatures are stated in degrees Centigrade; the parts are parts by weight.

EXAMPLE 1

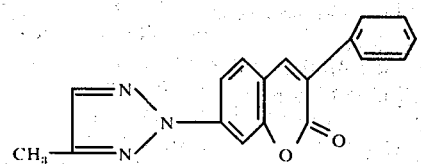

10 parts of hydrazone oxime of the formula II ($R_2=CH_3$, $R_1=R_3=H$) are dissolved in 30 parts of dimethylsulphoxide at 60°–70°. This solution is added in a single batch to a mixture at 60° consisting of 50 parts of acetic acid anhydride and 50 parts of pyridine. The mixture is brought to 100° while stirring and a brown, slightly cloudy solution is obtained which is then heated for 2 hours at 100° and subsequently boiled for 2 hours at reflux. On cooling the solution a crystalline precipitate forms which is filtered and washed with ethanol. After drying, 4.5 parts of yellow-brown leaflets are obtained having a melting point of 214°–220°. After reducing the volume of the mother liquor to half, a further 0.4 parts of brown leaflets of melting point 215°–220° are obtained giving a total yield of 51.8% of theory. By recrystallization from tetrachloroethylene (1:28) and treatment with charcoal the compound of the above formula is obtained in the form of slightly yellow crystals of melting point 217°–218°; these dissolve easily in chlorobenzene giving an intensive violet-blue fluorescence. (Found N: 13.9%; calculated for $C_{18}H_{13}N_3O_2$ N: 13.9%).

When the dimethylsulphoxide in this example is replaced with 30 parts of dimethylformamide or 30 parts of dimethylacetamide or 30 parts of N-methylpyrrolidone, there is obtained, after distilling off approximately 50% of liquid mixture, the same product in almost the same yield and purity.

The hydrazone oxime used in this Example was obtained starting from acetic acid ethyl ester by saponification, nitrosylation and reaction with 3-phenyl-7-hydrazinocoumarin. It is present in the form of a yellow, water insoluble powder of melting point 248°–250°.

EXAMPLE 2

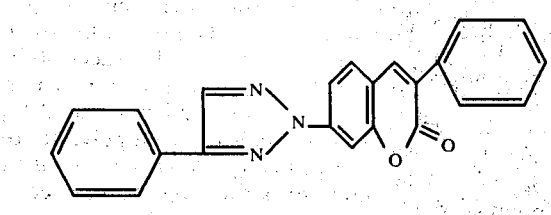

17 parts of hydrazone oxime of the formula II ($R_2$=phenyl, $R_1 = H$, $R_3 = H$) of melting point 208°–210° are dissolved at 70° in 51 parts of dimethylformamide and mixed in one batch with a mixture at 70° consisting of 85 parts of acetic acid anhydride and 85 parts of pyridine. The resulting material is first heated to 100° for 3 hours and then at the boil for 2 hours. Subsequently half of the liquid is distilled off at atmospheric pressure, cooling is allowed to take place and crystallization. The resulting coarsely crystalline precipitate is filtered off and washed well with ethanol. After drying, 8.55 parts (52.8% of theory) of orange-yellow crystals result having a melting point of 240°–242°. After recrystallization from chlorobenzene and treatment with charcoal, the compound of the above formula is obtained in the form of almost colourless crystals of melting point 241°–242°; these are soluble in organic solvents giving a luminous blue fluorescence.

When in the above hydrazone oxime $R_3$ is replaced with methyl, chlorine or methoxy (in 4-position), a product results with a similar good effect. These compounds are especially suitable as optical brighteners for masses of synthetic polymers for spinning and pressing.

EXAMPLE 3

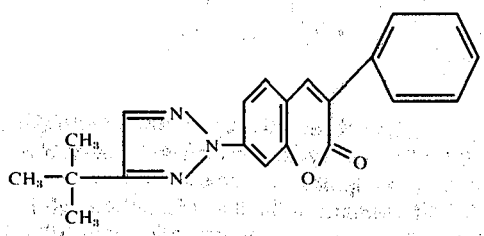

20 parts of hydrazone oxime of the formula II ($R_2$= tert.-butyl, $R_1 = H$, $R_3 = H$) of melting point 206°–210° are dissolved in 60 parts of dimethylformamide at 70° and united with a mixture, heated to 70°, consisting of 100 parts of acetic acid anhydride and 100 parts of pyridine. The resulting mixture is subsequently heated to 100° while stirring. After one hour the starting material has almost disappeared. Stirring is effected at 100° for 3–4 hours longer and about half the liquid is distilled off. On cooling of the brown solution a large amount of crystals precipitates out and these are washed with ethanol and dried. 9–10 parts of the compound of the above formula having a melting point of 198°–199° are obtained. By recrystallization from glacial acetic acid and treatment with a trace of zinc dust colourless crystals with an unchanged melting point of 198°–199° are obtained. When the acetic acid anhydride in this Example is replaced with 100 parts of propionic acid anhydride and the procedure is otherwise the same, the product of the above formula is obtained with about the same yield and purity. It is more easily soluble in organic solvents than the hitherto described compounds.

The solutions have a strong violet-blue fluorescence. Products with similar compounds are obtained when there is used as starting material a hydrazone oxime in which $R_3$ represents chlorine, methoxy, methyl or tert.-butyl, but the procedure is otherwise the same. When working in Examples 1, 2 and 3 is effected in the absence of pyridine, the same compounds as stated therein are obtained, but the yield is slightly lower.

EXAMPLE 4

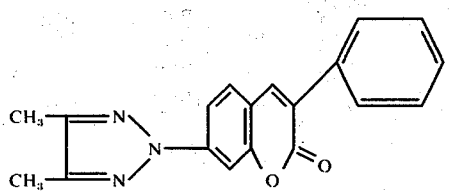

10 parts of hydrazone oxime of the formula II ($R_1 = R_2 = CH_3$, $R_3 = H$) of melting point 277°–280° are dissolved in 30 parts of dimethylacetamide, 50 parts of acetic acid anhydride and 50 parts of a mixture of pyridine bases are added and stirring is effected for 1 hour at 80° and then for 2 hours at 100°. subsequently boiling is effected for 2–3 hours (135°–140°), two-thirds of the liquid is distilled off and the remaining material is allowed to stand overnight. The fine crystalline precipitate resulting in this way is washed in the usual manner and recrystallized from tetrachloroethylene with the use of charcoal. A compound of the above formula in the form of pale yellow crystals of melting point 231°–232° results. When the dimethylacetamide of this Example is replaced with 30 parts of dimethylformamide or 30 parts of N-methylpyrrolidone, the same dimethyltriazole with similar yield and purity results. When the starting material of this Example is replaced with a hydrazone oxime in which $R_1$ is n-butyl and $R_2$ is methyl, the procedure being otherwise the same as described above, an almost colourless product of melting point 103°–104° results (found N: 11.5%; calculated for $C_{22}H_{21}N_3O_2$ N:11.7%).

When in the hydrazone oxime of Example 4 $R_3$ is replaced with p- or m-$CH_3$, p- or m-Cl, or p- or m-$OCH_3$, optical brighteners result which are similarly useful as there described.

EXAMPLE 5

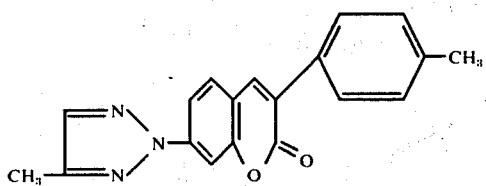

10 parts of hydrazone oxime of the formula II ($R_2=R_3=CH_3$, $R_1 = H$) are cyclized as in Example 1. The resulting light brown crystals are recrystallized from a mixture of chlorobenzene-glacial acetic acid (9:1) in the presence of zinc dust. A compound of the above formula in the form of slightly yellow crystals is obtained which is characterized by an especially strong blue fluorescence in organic solvents.

EXAMPLE 6

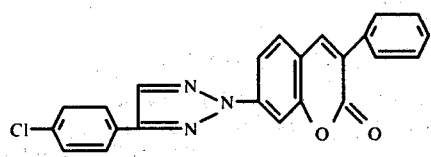

20 parts of hydrazone oxime of the formula II ($R_2$=p-chlorophenyl, $R_1 = H$, $R_3 = H$), which may be produced from p-chlorobenzoyl acetic acid ester in accordance with the procedure mentioned in Example 1, are cyclized as described in Example 3. The reaction product is purified by recrystallization from chlorobenzene and treatment with charcoal. A compound of the above formula as a pale yellow crystalline powder is obtained. A product with quite similar properties results when in the hydrazone oxime of this Example $R_2$ is replaced with p-tolyl, the procedure being otherwise the same. The compounds are as suitable as the already described ones for optically brightening organic materials.

EXAMPLE 7

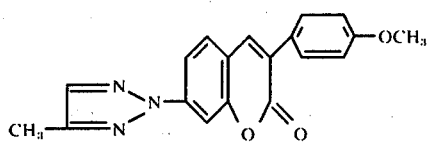

10 parts of hydrazone oxime of the formula II ($R_2=CH_3$, $R_1 = H$, $R_3 = OCH_3$) are cyclized as in Example 1. The crude product is purified by recrystallization from a mixture of chlorobenzene-glacial acetic acid (9:1) and treatment with zinc dust; a compound of the above formula results which is characterized by a very brilliant blue fluorescence on dissolving in chlorobenzene. Products with almost the same properties are obtained when in the hydrazone oxime of this Example $R_3$ is replaced with ethoxy or chlorine. The starting materials required are produced from acetic acid ethyl ester according to the above described method, using 3-p-methoxyphenyl-7-hydrazinocoumarin or 3-p-ethoxyphenyl-7-hydrazinocoumarin or 3-p-chlorophenyl-7-hydrazinocoumarin. They form yellow powders which are insoluble in water.

EXAMPLE 8

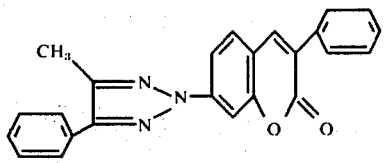

50 parts of hydrazone oxime of the formula II ($R_1 = CH_3$, $R_2 = $ phenyl, $R_3 = H$) are suspended in 100 parts of dimethylformamide and heated to 70°. A mixture consisting of 100 parts of acetic acid anhydride and 100 parts of pyridine, heated to 70°, is added in one batch to the suspension. After a few minutes a dark solution results which is stirred at 100° for 2 hours. The starting material has disappeared after that time. On cooling 29.1 parts (61% of theory) of reaction product of the above formula in the form of a fine light brown crystalline powder of melting point 161.5°–163° is obtained. After recrystallizing from glacial acetic acid and treatment with charcoal, the resulting new triazole compound melts at 162°–163°. It is relatively easily soluble in the usual solvents; in solution it shows an intensive blue fluorescence.

Quite similar compounds are obtained when in the above mentioned hydrazone oxime $R_2$ is replaced with p-tolyl or p-methoxyphenyl, $R_3$ with chlorine, methyl, isopropyl or t-butyl, the procedure being otherwise the same. All these compounds are highly suitable for optically brightening plastics.

A good yield of the above mentioned hydrazone oxime may be obtained by condensation of isonitrosopropiophenone with 3-phenyl-7-hydrazinocoumarin (yellow powder of melting point 285°–286° [decomposition]).

EXAMPLE 9

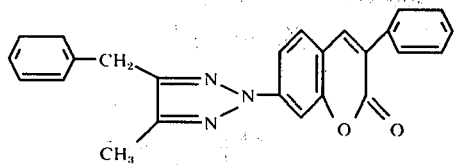

10 parts of hydrazone oxime of the formula II ($R_1$ = benzyl, $R_2 = CH_3$, $R_3 = H$) of melting point 265°–268° together with 30 parts of dimethylformamide, 50 parts of acetic acid anhydride and 50 parts of pyridine, are heated to 80°. A dark, slightly cloudy solution results which is stirred for 2 hours at this temperature and then for a further 2 hours at 100° and finally to boiling temperature. Subsequently about 50% of the volume of the resulting liquid mixture is distilled off. On cooling the reaction mixture the compound of the above formula separates out in the form of fine crystals. After washing with ethanol, the crystals are recrystallized from glacial acetic acid and treated with charcoal. The resulting new triazole compound melts at 169°–170°; dissolved in chlorobenzene it fluoresces with a strong violet-blue colour.

When there is used a hydrazone oxime of the formula II in which $R_1$=benzyl, $R_2$=$CH_3$ and $R_3$ is the methoxy or n-butoxy radical or a chlorine atom, the procedure being otherwise the same as described above, similarly valuable compounds are obtained which are eminently suitable for brightening plastics.

EXAMPLE 10

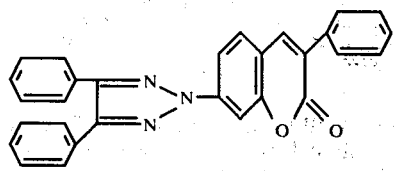

18 parts of hydrazone oxime of the formula II ($R_1$=phenyl, $R_2$=phenyl, $R_3$=H) are mixed with 36 parts of dimethylformamide, 54 parts of acetic acid anhydride and 54 parts of pyridine and cyclized and worked up as described in Example 8. Dirty whitish needles of melting point 203°–205° are obtained as crude product. After recrystallizing this material from 54 times the amount of glacial acetic acid and treatment with charcoal, practically colourless needles of melting point 213°–214° result; after dissolving these in chlorobenzene, a strong violet-blue fluoroescence is produced.

When in the above hydrazone oxime of the formula II the hydrogen atom of the radical $R_3$ is replaced with chlorine, methyl or t-butyl, compounds with similarly strong fluorescence result. All these new triazole compounds are especially suitable for brightening plastics spinning masses, especially for polyester spinning masses. The hydrazone oxime required as a starting material may be obtained, for example, from benzil by reaction with one mol of 3-phenyl-7-hydrazinocoumarin and subsequently converting to the oxime; melting point 238°–239° (decomposition); yield = 80–85%.

EXAMPLE 11

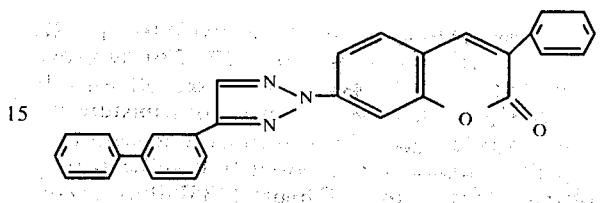

20 parts of hydrazone oxime of formula II ($R_1$=H, $R_2$=p-diphenyl, $R_3$=H) are mixed with 40 parts of dimethylformamide, 60 parts of acetic acid anhydride and 60 parts of pyridine and cyclized as in Example 8. After the cyclization is complete, about half of the solvent mixture material is distilled off and, on cooling of the reaction mixture, light brown crystals are obtained which are capable of purification by recrystallization from chlorobenzene and treatment with charcoal. The resulting compound of the above formula, when dissolved in chlorobenzene, shows a very strong, blue fluorescence.

When in the above hydrazone oxime, $R_2$ is styryl or p-chlorostyryl, the hydrogen atom $R_3$ is replaced with chlorine, methyl, methoxy, n-butoxy, isopropyl or t-butyl, the resulting compounds likewise fluoresce with a strong blue colour when dissolved; they are extremely suitable for optically brightening plastics.

EXAMPLE 12

50 parts of a hydrazone oxime, which is obtained from 2-isonitrosocyclopentanone(1) and 7-hydrazino-3-phenylcoumarin, are cyclized as in Example 8. The resulting compound has the formula

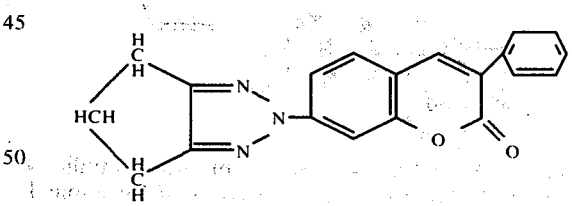

and is a brightening agent for plastics and spinning masses; its melting point is 281°–282°.

When the above 2-isonitrosocyclopentanone(1) is replaced with 2-isonitrosocyclohexanone(1) or 2-isonitrosotetralone(1) or 2-isonitrosoindanone(1), the procedure being otherwise the same, there are obtained brightening agents having properties quite similar to those of the compound having the formula shown in this Example.

EXAMPLE 13

10 parts of the compound described in Example 1 are mixed with 2 parts of castor oil which has been sulphonated to a high degree and is available commercially under the name of Sandozol KB (Trade Mark registered by the firm Sandoz), 8 parts of the sodium salt of dioctylphenylpolyglycol ether hydroxy acetic acid containing 40 ethenoxy radicals per molecule, and 80 parts of water, and the mixture is worked in a comminuting apparatus, for example in a sand mill, until the majority of the mass has a particle size of 0.5–2 μ. 100 parts of a fabric of poly-(ethyleneglycolterephthalate) are placed into a bath at 50°, which has the following composition: 3000 parts of water, 5 parts of o-dichlorobenzene as carrier and 2 parts of the above described dispersion. The material is left for 15 minutes at that temperature and the bath is then heated to boiling temperature during 30 minutes, boiling is continued for 45 minutes and the fabric is treated at 70° in a bath containing 1.5 g/l octylphenyldecaglycol ether (bath ratio 1:40, duration 10 minutes). Warm rinsing and drying are then effected. The polyester fabric treated in this way is strongly brightened. The brightening is characterized by a very good stability to light and washing. When working is effected at 120°–130° in closed apparatus, a similar white effect is achieved without addition of a carrier.

EXAMPLE 14

A mixed fabric of cotton/polyester, for example cotton/Diolen, is impregnated at room temperature by padding with a liquid containing 20 parts of the optical brightener dispersion described in Example 8 in 1000 parts of water. The liquid taken up is reduced to 80% by squeezing, drying for 30 minutes at 60° is effected and thermal treatment for one minute at 180° is effected. The fabric becomes strongly brightened by this procedure, the degree of brightening being similar to that described in Example 8. When there is used instead of the mixed fabric of this Example a polyester fabric (e.g. Dacron, Terylene or Diolen), the last mentioned fabric is brightened in manner similar to that for the mixed fabric.

EXAMPLE 15

A granulate of 6-polyamide (Grilon) is powdered in a mixing apparatus with 0.01–0.05% of its own weight of the compound described in Example 4 and melted in an apparatus usual for melt spinning for 30 minutes at about 300° under an atmosphere of nitrogen, stirred at that temperature for 15 minutes and then brought to the spinning temperature of 285°. At a pressure of 4–6 atmospheres (nitrogen) this mass is spun into a monofil. The resulting fibres fluoresce intensively blue in daylight. They appear whiter and brighter than fibres produced under comparable conditions but without brightener. When using, instead of the compound described in Example 4, those of Examples 1 or 2, similar white effects are produced. When using polyester or polypropylene, instead of polyamide, and spinning is effected at 290° and 260° respectively, there are likewise obtained fibres of a higher degree of whiteness than comparative fibres produced without brightener.

EXAMPLE 16

100 parts of polyester fabric, for example Diolen, are treated at 50°–95° for one and a half hours in a bath containing 3000 parts of water, 6 parts of formic acid (85%), 6 parts of sodium chlorite (80%), 5 parts of a carrier (for example Dilatin TC of Sandoz AG.) and 2 parts of the dispersion described in Example 8. Subsequently the fabric is washed, rinsed and dried as stated in Example 8. It has a higher degree of whiteness than a comparative sample bleached under otherwise the same conditions but without addition of the triazole derivative.

EXAMPLE 17

100 parts of polyvinyl chloride are dissolved in a usual solvent, for example methylene chloride, 0.04% of its weight of the brightener described in Example 2 and dissolved in the same solvent are added and spinning according to the wet spinning process is effected to produce threads. The product is markedly brightened and has an excellent stability to light in comparison to threads spun without brightener.

EXAMPLE 18

100 parts of polypropylene granulate are powdered in a mixing apparatus with 0.02–0.06 parts of brightener obtained according to Example 4; working up at 140°–220° is effected in a rolling mill and either pressed to form plates or regranulated and pressed to give shaped articles by spray casting. The resulting products have markedly improved degree of whiteness as compared to materials produced without brightener. The polypropylene may be replaced with high or low pressure polyethylene or with another polyolefin.

Similar brightening effects are obtained when a brightener produced according to Example 8 is used instead of the one mentioned above and produced according to Example 4.

EXAMPLE 19

100 parts of polyvinyl chloride mass (consisting of 65 parts polyvinyl chloride, 35 parts of a softener and 2%, based on the polymer, of a stabilizer) are mixed with 0.05–0.1 part of the brightener obtained according to Example 3 (the brightener is dissolved in the softener), working up on a rolling mill is effected at 150°–160° for 10 minutes and the resulting material is drawn to form foils. In order to produce opaque foils, 2.5% of titanium dioxide had been added to the mass before working up. The resulting foils have an improved appearance as compared with similar ones produced without brightener.

EXAMPLE 20

10 parts of polyacrylonitrile fabric, for example Orlon, are placed, at 60°, in a bath consisting of 300 parts of water, 0.6 parts of sodium chlorite, 0.3 parts of glacial acetic acid and 0.3–0.5 parts of the dispersion described in Example 8. Heating to 98°–100° for 20 minutes is effected and this temperature maintained for 60 minutes; cooling to 70°, warm rinsing, treatment at 60°–70° for 10 minutes with a sodium bisulphite solution (1 g/l) and again rinsing are effected. The dried fabric is more beautiful and whiter than one bleached under otherwise similar conditions but without the addition of triazole derivative.

Although the present invention is described herein with particular reference to specific details, it is not intended that such details shall be regarded as limitations upon the scope of the invention except insofar as included in the accompanying claims.

We claim:

1. A compound having the formula

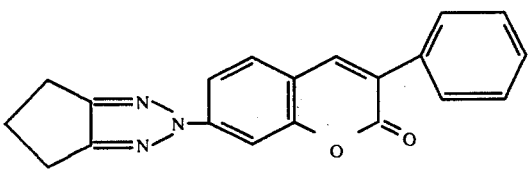

* * * * *